(12) United States Patent
Bussard et al.

(10) Patent No.: US 6,788,424 B1
(45) Date of Patent: Sep. 7, 2004

(54) OPTICAL FREQUENCY DISCRIMINATOR

(75) Inventors: Paul E Bussard, Santa Rosa, CA (US); Mark D Zinser, Vancouver, WA (US); James R Stimple, Santa Rosa, CA (US); Jeffrey Elmer Pape, Santa Rosa, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/427,613

(22) Filed: Apr. 30, 2003

(51) Int. Cl.[7] .................................................. G01B 9/02
(52) U.S. Cl. ...................................... 356/519; 356/454
(58) Field of Search .................................. 356/450, 451, 356/519, 454; 372/20, 19, 98, 32

(56) References Cited

U.S. PATENT DOCUMENTS

| | | | |
|---|---|---|---|
| 5,426,502 A | * 6/1995 | Miyata et al. | ............... 356/477 |
| 6,249,343 B1 | 6/2001 | Wang et al. | |
| 6,421,120 B1 | * 7/2002 | Wildnauer | ............... 356/243.1 |
| 6,567,433 B2 | * 5/2003 | May | ............................ 372/20 |

* cited by examiner

*Primary Examiner*—Frank G. Font
*Assistant Examiner*—Andrew H. Lee
(74) *Attorney, Agent, or Firm*—John L. Imperato

(57) ABSTRACT

An optical frequency discriminator includes an interferometer cascaded with an absorption cell that provide a composite signal. A receiver samples a composite signal and maps to the sample positions of the acquired samples, corresponding optical frequencies of an applied optical signal.

12 Claims, 4 Drawing Sheets

OPTICAL FREQUENCY DISCRIMINATOR

BACKGROUND OF THE INVENTION

Determining the frequency of an optical signal is desirable in a variety of measurement environments. For example, determining the frequency of an optical signal applied to a measurement receiver enables the frequency scale of the measurement receiver to be calibrated, whereas determining the frequency of an optical signal from an optical source enables the frequency tuning characteristics of the optical source to be calibrated.

Absorption cells are often used when determining the frequency of an optical signal. These absorption cells are typically gas cells that contain one or more gases, such as acetylene and methane, or hydrogen cyanide, and provide absorption lines at optical frequencies that are spaced over a broad frequency range. The absorption lines are stable over time and stable over a variety of environmental conditions, making the absorption cells well-suited frequency standards in optical frequency determinations.

U.S. Pat. No. 6,249,343 B1 to Wang et al. discloses an absorption cell configured to frequency calibrate a measurement receiver, such as an optical spectrum analyzer. Alternatively, absorption cells can be configured to frequency calibrate optical sources, such as a tuneable laser source, as shown in FIG. 1. In FIG. 1, the absorption cell is illuminated by the tuneable laser source while a broadband receiver, such as an optical network analyzer or power meter, detects a resultant optical signal at the output of the absorption cell. Since optical energy is absorbed at frequencies precisely defined by the absorption lines of the absorption cell, the frequency of the tuneable laser source can be accurately determined at those frequencies by observing the position of amplitude notches or minima detected in the frequency response measured by the receiver. While determining optical frequency at various frequency positions—including those between the absorption lines, is critical for characterizing optical sources that have nonlinear tuning characteristics, or for optical signals in dispersive media, the prior art configuration shown in FIG. 1 does not readily enable accurate frequency determinations to be made at frequency positions other than those of the absorption lines. Accordingly, there is a need for a frequency discriminator that enables the frequency of an applied optical signal to be determined not only at the absorption lines of an absorption cell, but also at frequency positions between absorption lines.

SUMMARY OF THE INVENTION

An optical frequency discriminator constructed according to the embodiments of the present invention includes an interferometer cascaded with an absorption cell. In response to an applied optical signal, the cascaded arrangement provides a composite signal that is a superimposition of a cyclical fringe signal provided by the interferometer and a series of absorption lines provided by the absorption cell. A receiver samples the composite signal and maps sample positions of the acquired samples and corresponding optical frequencies of the optical signal, based on the cycles of the fringe signal and identified frequencies of predesignated absorption lines in the series. Alternative embodiments of the present invention are directed toward an optical frequency discrimination method.

DETAILED DESCRIPTION

Figure 1:
FIG. 1 shows a prior art optical frequency calibrator.
Figure 2:
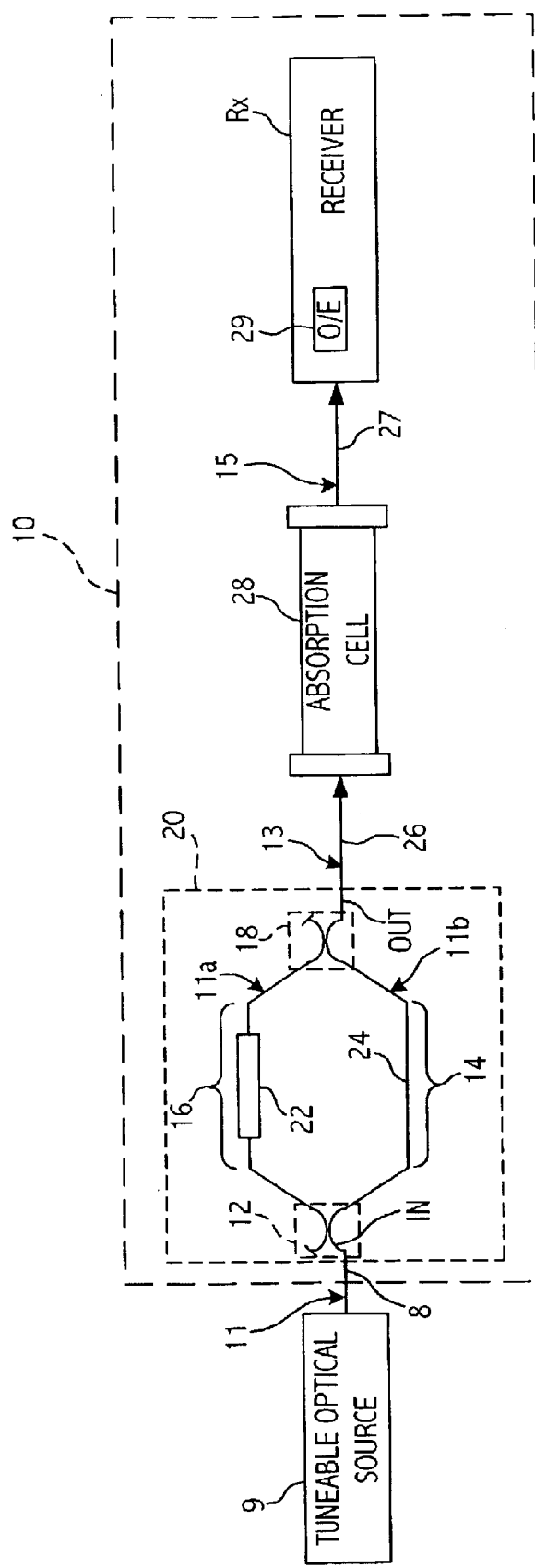
FIG. 2 shows an optical frequency discriminator constructed according to embodiments of the present invention.

FIG. 2 shows an optical frequency discriminator 10 constructed according to embodiments of the present invention. Although the term "frequency" is used throughout, frequency and wavelength are interchangeable due to the inherent reciprocal relationship between frequency and wavelength. The optical frequency discriminator 10 includes a splitter 12 that is coupled to a tuneable optical source 9, typically a TLS (tuneable laser source) via a fiber 8 or other type of transmission path including various optical elements or transmission media (not shown). The tuneable optical source 9 is a polarized optical source, such as an AGILENT TECHNOLOGIES, INC. Model 81640B, that is tuneable in optical frequency. The tuneable optical source 9 provides an optical signal 11 to the splitter 12. The splitter 12 divides the optical signal 11 between a reference path 14 and a delay path 16. The reference path 14 and the delay path 16 are recombined at a combiner 18. A first output from splitter 12 is coupled to a first input of the combiner 18 by a fiber 22, whereas a second output from splitter 12 is coupled to a second input of the combiner 18 by a fiber 24. In this example, the optical path length difference between the reference path 14 and the delay path 16 is designated to be 0.25 meters, however other optical path length differences are alternatively employed.

Together, the splitter 12, the reference path 14, the delay path 16, and the combiner 18 form a Mach-Zehnder interferometer 20. As alternatives to the Mach-Zehnder interferometer, the optical frequency discriminator 10 includes another type of interferometer, for example a Fabry-Perot interferometer or Michelson interferometer.

A sinusoidal interference pattern in the form of a fringe signal 13 results at the output OUT of the interferometer 20 in response to the optical signal 11. The fringe signal 13 has sufficient contrast, provided that the polarizations of optical signals 11a, 11b combined at the output OUT are not orthogonal; as the contrast of the fringe signal 13 generally increases as the polarizations of the optical signals 11a, 11b become more aligned.

The optical frequency discriminator 10 includes an absorption cell 28 cascaded with the interferometer 20 in a series arrangement via a fiber 26 at the output OUT as shown in FIG. 2, or at the input IN, between the tuneable optical source 9 and the splitter 12 (not shown). The absorption cell 28 typically includes one or more gas cells that contain one or more gases, such as acetylene, methane, or hydrogen cyanide, for example, and provides optical absorption lines 17 (shown in FIG. 3) at frequencies that are spaced over a broad frequency range. In one example the interferometer 20 is a Fabry-Perot interferometer and the cascade of the interferometer 20 and the absorption cell 28 includes the Fabry-Perot interferometer, such as a JDS UNIPASE WVL-2B10 BROADBAND WAVELENGTH LOCKER, enclosed within the absorption cell 28.

The absorption lines 17 are stable over time and stable over a variety of environmental conditions, making the absorption cell 28 a well-suited frequency standard. Characteristics of suitable absorption cells 28 are known in the art. An example showing the absorption lines 17 of an absorption cell is provided in U.S. Pat. No. 6,249,343 B1 to Wang et al.

In response to the optical signal 11 applied to the optical frequency discriminator 10, the cascaded arrangement of the interferometer 20 and the absorption cell 28 provides a composite signal 15 that includes a superposition of the fringe signal 13 provided by the interferometer 20, and the absorption lines 17 provided by the absorption cell 28. The composite signal 15, including the fringe signal 13 and the absorption lines 17 (shown in the exemplary plots of FIG. 3), is applied to a receiver Rx. In the example where the interferometer 20 is a Mach-Zehnder interferometer as shown, sufficient polarization alignment is achieved by adjusting the mounting of the fibers 22, 24, or by implementing the splitter 12 and the combiner 18 using polarization-maintaining couplers and implementing the fibers 22, 24 using polarization-maintaining fibers. Typically, the coupling ratio of each of the splitter 12 and/or combiner 18 are staggered, for example 10% and 90% coupling ratios between the reference path 14 and the delay path 16, to prevent the intensity of the composite signal 15 from dropping below a predesignated minimum intensity when the fringe signal 13 and the absorption lines 17 are superimposed.

The receiver Rx digitizes, records, measures, or otherwise samples the composite signal 15 over time, where positions of the samples in time are represented by sample number, or index i. In one example, the receiver Rx is a network analyzer combined with an optical-to-electrical (O/E) converter 29, where the composite signal 15 is coupled to the network analyzer via a fiber 27. Alternatively, the receiver Rx is an optical power meter or other broadband optical detector suitable for sampling the composite signal 15.

When the tuneable optical source 9 providing the optical signal 11 does not have consistent or repeatable frequency tuning or sweep characteristics, or when characteristics of optical components in the optical transmission path are time-varying, sampling the composite signal 15 over a single frequency sweep of the optical signal 11 is advantageous to provide a representative mapping between the sample positions i and corresponding optical frequencies $\omega(i)$ of the optical signal 11.

Figure 3:
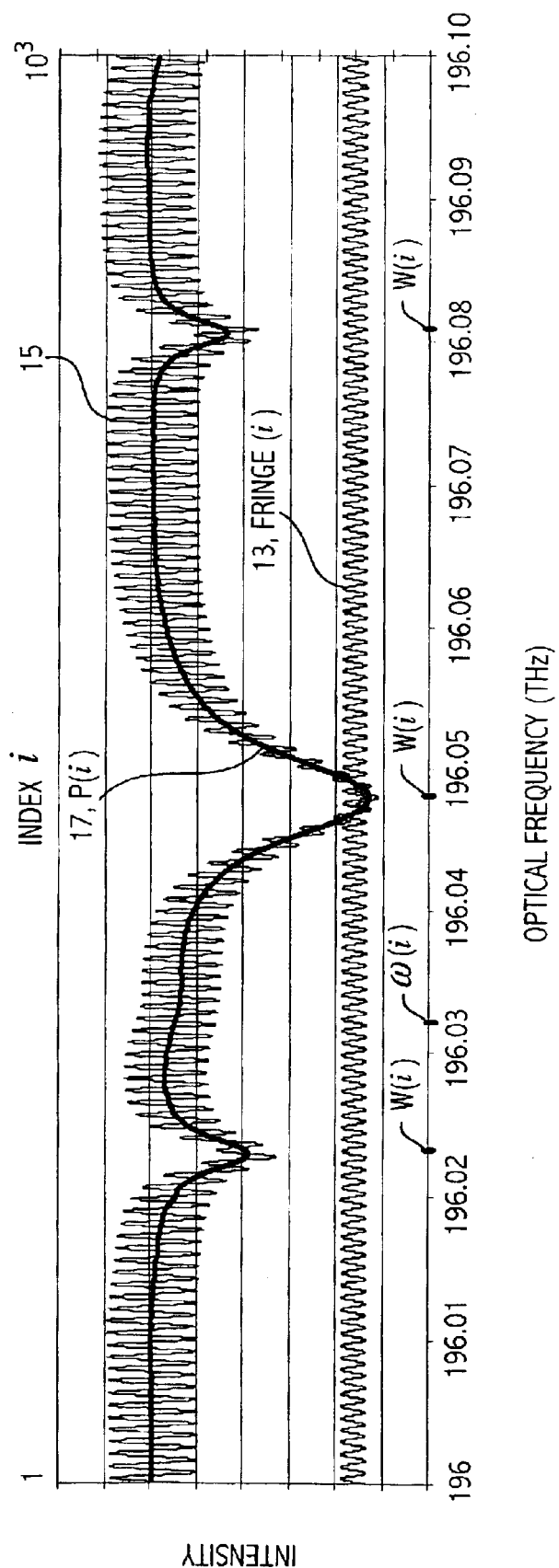
FIG. 3 shows exemplary signals provided by the frequency discriminator constructed according to the embodiments of the present invention.

The mapping between optical frequencies $\omega(i)$ and the sample positions, or indices i, includes isolating the fringe signal 13 from the absorption lines 17 in the composite signal 15, typically by filtering the sampled representation of the composite signal 15 to separate samples representing the fringe signal 13 from samples representing the absorption lines 17. This isolation is conveniently performed using a digital filter, being that the fringe signal 13 is sinusoidal and is readily separable from the spectral characteristics of the absorption lines 17 and the sampled representation of the composite signal 15 is typically in digital form. This isolation results in a sampled representation P(i) of the absorption lines 17 and the sampled representation FRINGE(i) of the fringe signal 13. The exemplary signals in FIG. 3 show the fringe signal 13, the absorption lines 17, and the composite signal 15 versus optical frequency, and also show the sampled representation P(i) of the absorption lines 17 and the sampled representation FRINGE(i) of the fringe signal 13 versus indices, or sample positions i.

The frequencies of designated absorption lines 17 in the series of absorption lines are then identified, typically by identifying magnitude minima or notches in the sampled representation P(i) of the absorption lines 17 based on center of mass calculations, or curve fitting techniques applied to the sampled representation P(i). This results in an accurate mapping of sample positions i that are proximate to the absorption lines 17 to the optical frequencies W(i) of the absorption lines 17. For example, where the absorption cell 28 includes one gas cell containing Acetylene ($^{12}C_2H_2$) and Methane ($CH_4$), and another gas cell containing Hydrogen Cyanide ($H^{13}C^{14}N$), a center of mass of a magnitude minimum that is within 3.75 GHz of an absorption line is associated with the known frequency of the absorption line. In this example, where the absorption lines 17 span the optical frequency range of 183.0416 THz to 198.1181 THz with 76 points, sample positions i proximate to the absorption lines 17 in the sampled representation P(i) are mapped to the optical frequencies W(i) of the absorption lines 17 with an uncertainty of less than +/−75 MHz.

The sampled representation FRINGE(i) of the fringe signal 13 resulting from the isolation of the fringe signal 13 from the absorption lines 17 represents the cyclical interference pattern of the fringe signal 13. Cycles of the fringe signal 13 have slight frequency deviations when optical elements or transmission media in the optical transmission paths of the optical frequency discriminator 10, are dispersive. This dispersion is accommodated for in the mapping between sample positions i and the optical frequencies $\omega(i)$.

In one example, the sample positions i and the corresponding optical frequencies $\omega(i)$ are mapped by counting the number of cycles, or fringes, in the sampled representation FRINGE(i) that occur between the identified frequencies W(i) of the designated absorption lines 17. Interpolation based on the number of cycles that occur between the identified optical frequencies W(i) at the sample points proximate to the absorption lines 17 provides the mapping between the corresponding optical frequencies $\omega(i)$ and the sample numbers i that lie between the identified optical frequencies W(i) of the absorption lines 17.

In another example, an accumulated phase $\phi(i)$ is assigned to the sample positions i in the sampled representation FRINGE(i) of the fringe signal 13 on the basis that each cycle of the interference pattern results in a phase increase of $2\pi$, radians. Then, interpolation based on a piecewise linear representation of the accumulated phase $\phi(i)$ versus the identified optical frequencies W(i) is used to map each sample number i to the corresponding optical frequencies $\omega(i)$ of the optical signal 11.

In yet another example, interpolation is based on a curve fit of the accumulated phase $\phi(i)$ to the identified optical frequencies W(i) of the absorption lines 17. Then, each sample position i is mapped to a corresponding optical frequency $\omega(i)$ within the frequency sweep of the optical signal 11 based on the curve fit. When sufficient degrees of freedom are provided in the curve fit, for example by using a sufficiently high order polynomial in the example of a polynomial curve fit, this approach accommodates phase nonlinearities that result from dispersion or other phase nonlinearities of the tuneable optical source 9.

Figure 4:
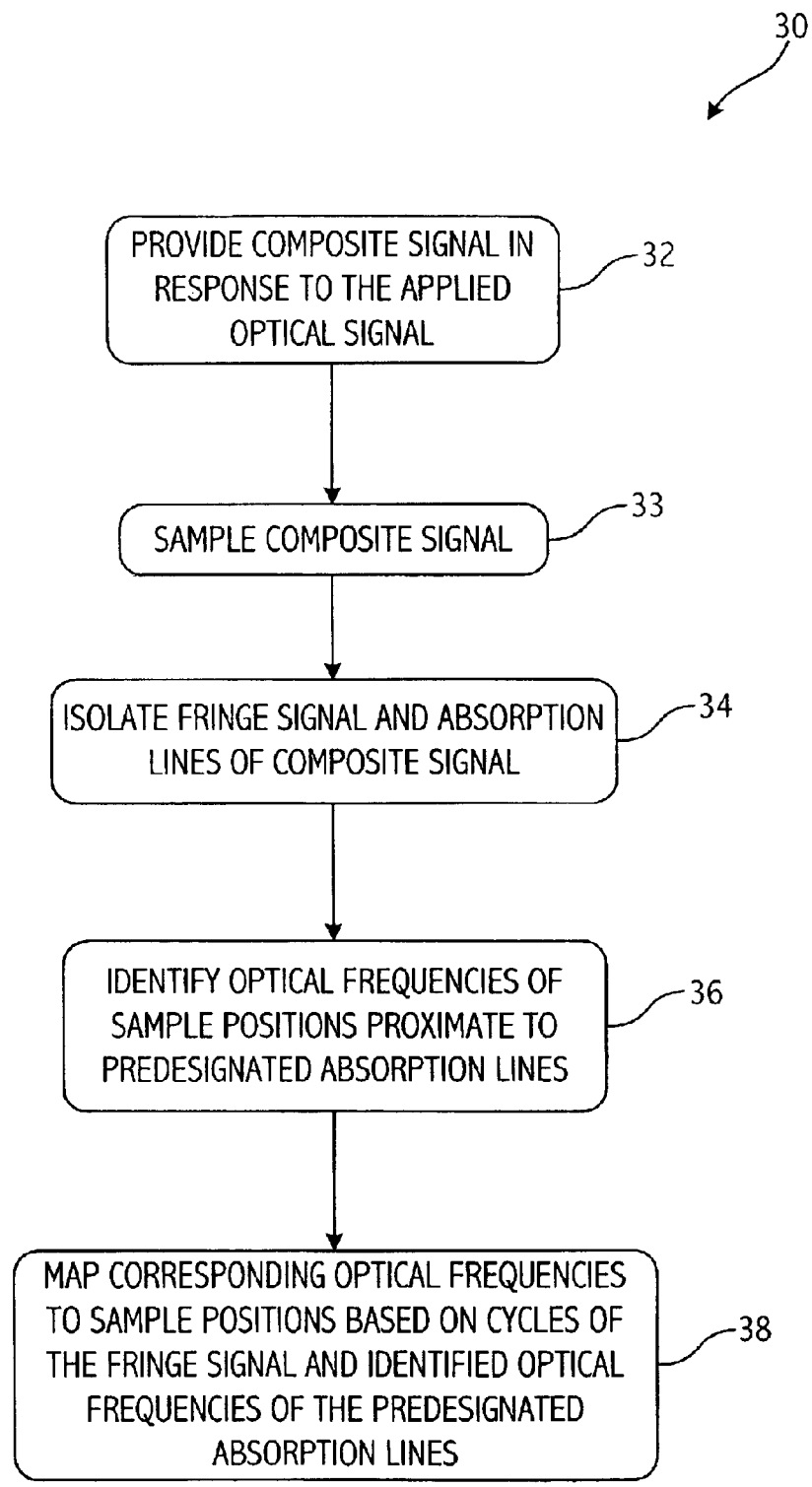
FIG. 4 is a flow diagram of an optical frequency discrimination method in accordance with alternative embodiments of the present invention.

Alternative embodiments of the present invention are directed toward an optical frequency discrimination method 30 shown in the flow diagram of FIG. 4. Step 32 of the method 30 shows the composite signal 15 being provided in response to the applied optical signal 11, where the composite signal 15 is a superposition of the series of absorption lines 17 and the fringe signal 13. In step 33, the composite signal 15 is sampled. In step 34, the fringe signal 13 and the absorption lines 17 of the composite signal 15 that was sampled in step 32 are isolated, resulting in the sampled representation P(i) of the absorption lines 17 and the sampled representation FRINGE(i) of the fringe signal 13. In step 36, the optical frequencies W(i) of the sample positions i proximate to the absorption lines 17 in the sampled representation P(i) are identified. In step 38, sample positions i are mapped to optical frequencies ω(i) that correspond to the optical signal 11, based on cycles of the fringe signal 13 and the identified optical frequencies W(i) of the absorption lines 17. This mapping is according to interpolations based on the number of cycles in the sampled representation FRINGE(i) of the fringe signal 13 that lie between the identified optical frequencies. Typically, the interpolations are based on a piecewise linear representation of the accumulated phase φ(i) versus the identified optical frequencies W(i) or the interpolations are based on a curve fit of the accumulated phase φ(i) to the optical frequencies W(i).

While the embodiments of the present invention have been illustrated in detail, it should be apparent that modifications and adaptations to these embodiments may occur to one skilled in the art without departing from the scope of the present invention as set forth in the following claims.

What is claimed is:

1. An optical frequency discriminator, comprising:
   an interferometer;
   an absorption cell cascaded with the interferometer, the absorption cell having a series of characteristic absorption lines, wherein the cascaded interferometer and absorption cell include a Fabry-Perot interferometer within the absorption cell; and
   a receiver coupled to the cascaded interferometer and the absorption cell.

2. An optical frequency discriminator, comprising:
   an interferometer receiving an optical signal and providing a fringe signal in response to the received optical signal;
   an absorption cell cascaded with the interferometer having a series of characteristic absorption lines, the cascaded interferometer and absorption cell forming a composite signal being a superposition of the fringe signal and the series of absorption lines; and
   a receiver sampling the composite signal and mapping a corresponding optical frequency within a frequency sweep of the optical signal to each of one or more sample positions of the sampled composite signal based on cycles of the fringe signal and identified optical frequencies of predesignated absorption lines within the series of absorption lines, the receiver isolating the fringe signal from the predesignated absorption lines and determining the number of cycles of the fringe signal between the predetermined absorption lines.

3. The optical frequency discriminator of claim 2 wherein mapping a corresponding optical frequency to each of the one or more sample positions includes an interpolation based the determined number of cycles of the fringe signal between the predetermined absorption lines.

4. The optical frequency discriminator of claim 2 wherein mapping a corresponding optical frequency each of the one or more sample positions includes assigning an accumulated phase to the each of the one or more sample positions and establishing a piece-wise linear representation of the accumulated phase versus the identified optical frequencies of the predesignated absorption lines.

5. The optical frequency discriminator of claim 2 wherein mapping a corresponding optical frequency to each of the one or more sample positions includes assigning an accumulated phase to the each of the one or more sample positions and establishing a curve fit of the accumulated phase and the identified optical frequencies of the predesignated absorption lines.

6. An optical frequency discrimination method, comprising:
   providing a composite signal based on a frequency sweep of an optical signal, the composite signal including a fringe signal and a series of absorption lines;
   sampling the composite signal;
   isolating the fringe signal from the series of absorption lines represented in the sampled composite signal;
   identifying the optical frequency of predetermined absorption lines in the series; and
   mapping a corresponding optical frequency within the frequency sweep of the optical signal to each of one or more sample positions based on a determined number of cycles of the fringe signal occurring and the identified optical frequencies of the predesignated absorption lines.

7. The optical frequency discrimination method of claim 6 wherein providing the composite signal based on a frequency sweep of the optical signal includes receiving a frequency sweep of the optical signal, dividing the optical signal between a reference path and a delay path, combining the reference path and the delay path to provide a fringe signal and superimposing a series of absorption lines on the fringe signal.

8. The optical frequency discrimination method of claim 6 wherein sampling the composite signal includes sampling the magnitude of the composite signal.

9. The optical frequency discrimination method of claim 6 wherein mapping a corresponding optical frequency within a frequency sweep of the optical signal to each of one or more samples includes interpolating based on the determined number of cycles of the fringe signal and the identified optical frequencies of the predesignated absorption lines.

10. The optical frequency discrimination method of claim 6 wherein mapping a corresponding optical frequency each of the one or more sample positions includes assigning an accumulated phase to the each of the one or more sample positions and establishing a piece-wise linear representation of the accumulated phase versus the identified optical frequencies of the predesignated absorption lines.

11. The optical frequency discrimination method of claim 6 wherein mapping a corresponding optical frequency to each of the one or more sample positions includes assigning an accumulated phase to the each of the one or more sample positions and establishing a curve fit of the accumulated phase and the identified optical frequencies of the predesignated absorption lines.

12. The optical frequency discrimination method of claim 7 wherein mapping a corresponding optical frequency to each of the one or more sample positions includes assigning an accumulated phase to the each of the one or more sample positions and establishing a curve fit of the accumulated phase and the identified optical frequencies of the predesignated absorption lines.

* * * * *